United States Patent [19]

Zale et al.

[11] Patent Number: 5,674,534
[45] Date of Patent: Oct. 7, 1997

[54] COMPOSITION FOR SUSTAINED RELEASE OF NON-AGGREGATED ERYTHROPOIETIN

[75] Inventors: Stephen E. Zale, Hopkington; Paul A. Burke, Medford; Howard Bernstein, Cambridge; Avram Brickner, Brookline, all of Mass.

[73] Assignee: Alkermes, Inc., Cambridge, Mass.

[21] Appl. No.: 483,318

[22] Filed: Jun. 7, 1995

Related U.S. Application Data

[63] Continuation-in-part of Ser. No. 885,307, Jun. 11, 1992, abandoned.

[51] Int. Cl.$^6$ .............. A61K 9/50; B32B 5/16; B01J 13/02
[52] U.S. Cl. .............. 424/501; 424/502; 264/4.6; 428/402.2; 428/402.21
[58] Field of Search .............. 264/4.6; 428/402.2, 428/402.21; 424/491, 497, 501, 502

[56] References Cited

U.S. PATENT DOCUMENTS

| | | | |
|---|---|---|---|
| 4,637,905 | 1/1987 | Gardner | 264/4.3 |
| 4,675,189 | 6/1987 | Kent et al. | 424/490 |
| 4,711,782 | 12/1987 | Okada et al. | 424/455 |
| 4,732,889 | 3/1988 | Cynshi et al. | 514/8 |
| 4,767,628 | 8/1988 | Hutchinson | 424/426 |

(List continued on next page.)

FOREIGN PATENT DOCUMENTS

| | | |
|---|---|---|
| 0537559 A1 | 10/1992 | European Pat. Off. . |
| WO 90/09166 | 8/1990 | WIPO . |
| WO 90/13780 | 11/1990 | WIPO . |
| WO 92/11844 | 7/1992 | WIPO . |
| WO 91/12882 | 9/1992 | WIPO . |
| WO 93/07861 | 4/1993 | WIPO . |
| WO 93/17668 | 9/1993 | WIPO . |
| WO 93/25221 | 12/1993 | WIPO . |
| WO 94/12158 | 6/1994 | WIPO . |
| WO 96/07399 | 3/1996 | WIPO . |

OTHER PUBLICATIONS

Costantino, H. R., et al., "Solid–Phase Aggregation of Proteins under Pharmaceutically Relevant Conditions," *Journal of Pharmaceutical Sciences*, 83(12): 1662–1669 (1994).

Costantino, H. R., et al., "Moisture–Induced Aggregation of Lyophilized Insulin," *Pharmaceutical Research*, 11(1): 21–29 (1994).

Costantino, H. R., et al., "Aggregation of a Lyophilized Pharmaceutical Protein, Recombinant Human Albumin: Effect of Moisture and Stabilization by Excipients," *Biotechnology*, 13: 493–496 (1995).

Creighton, T. E., "Physical Forces That Determine the Properties of Proteins," In *Proteins, Structures and Molecular Principles*, (NY: W. H. Freeman and Company), pp. 149–150.

*Primary Examiner*—Carlos A. Azpuru
*Attorney, Agent, or Firm*—Hamilton, Brook, Smith & Reynolds, P.C.

[57] ABSTRACT

A composition, and methods of forming and using said composition, for the sustained release of non-aggregated, biologically active, erythropoietin (EPO). The sustained release composition of this invention comprises a polymeric matrix of a biocompatible polymer and particles of biologically active, aggregation-stabilized EPO, wherein said particles are dispersed within the biocompatible polymer. The method of the invention for producing a composition for the sustained release of biologically active EPO, includes dissolving a biocompatible polymer in a polymer solvent to form a polymer solution, dispersing particles of biologically active, aggregation-stabilized EPO in the polymer solution, and then solidifying the polymer to form a polymeric matrix containing a dispersion of said EPO particles. The method for using a composition of the invention is a method for providing a therapeutically effective blood level of biologically active, non-aggregated erythropoietin in a subject for a sustained period. In this method, a subject is administered an effective dose of the sustained release composition of the present invention.

29 Claims, 4 Drawing Sheets

U.S. PATENT DOCUMENTS

| | | | |
|---|---|---|---|
| 4,879,272 | 11/1989 | Shimoda et al. | 514/8 |
| 4,891,225 | 1/1990 | Langer et al. | 424/428 |
| 4,897,268 | 1/1990 | Tice et al. | 424/422 |
| 4,906,474 | 3/1990 | Langer et al. | 424/428 |
| 4,962,091 | 10/1990 | Eppstein et al. | 514/2 |
| 4,981,696 | 1/1991 | Loomis et al. | 424/486 |
| 4,992,419 | 2/1991 | Woog et al. | 514/8 |
| 5,019,400 | 5/1991 | Gombotz et al. | 424/497 |
| 5,126,147 | 6/1992 | Silvestri et al. | 424/497 |
| 5,192,741 | 3/1993 | Orsolini et al. | 514/4 |

COMPOSITION FOR SUSTAINED RELEASE OF NON-AGGREGATED ERYTHROPOIETIN

RELATED APPLICATIONS

This application is a Continuation-in-Part of U.S. patent application Ser. No. 07/885,307, filed Jun. 11, 1992, now abandoned, which is incorporated herein by reference in its entirety.

BACKGROUND OF THE INVENTION

Erythropoietin (EPO) is a glycoprotein, which can be isolated from urine or produced by recombinant genetic engineering, which is used as a hematinic to increase red blood cell count in a recipient.

Normal production of red blood cells requires the secretion of EPO by the kidneys. The EPO triggers proliferation and differentiation of a population of receptive stem cells in the bone marrow, stimulates hemoglobin synthesis in maturing erythroid cells, and accelerates release of red blood cells from the bone marrow into circulation, thereby increasing the red blood cell mass.

EPO is typically used to treat patients with anemia, particularly wherein the anemia is associated with renal failure. Currently, aqueous EPO is administered as a subcutaneous or intravenous bolus three times a week to patients to maintain suitable serum levels of EPO.

For patients chronically receiving EPO, the frequent injections result in significant variations in serum EPO levels, as well as patient compliance problems.

To resolve the problems associated with repetitive injections of aqueous EPO, attempts have been made to formulate controlled release devices containing higher doses of EPO than a bolus injection, encapsulated within a polymer and/or protein, wherein the EPO would be released in vivo over a period of about a week or more.

However, these controlled release devices typically exhibited high initial bursts of EPO release and minimal EPO release thereafter. Further, due to the high concentration of EPO within these controlled release devices, the EPO molecules (monomer) have tended to aggregate after several days to form aggregated EPO which, unlike EPO monomer, is immunogenic in vivo.

Therefore, a need exists for a means for sustaining the release of biologically active EPO in vivo without causing an immune system response over the release period of the EPO.

SUMMARY OF THE INVENTION

This invention relates to a composition, and methods of forming and using said composition, for the sustained release of non-aggregated, biologically active erythropoietin (EPO). The sustained release composition of this invention comprises a polymeric matrix of a biocompatible polymer and particles of biologically active, aggregation-stabilized EPO, wherein said particles are dispersed within the biocompatible polymer.

The method of the invention for forming a composition for the sustained release of non-aggregated EPO, includes dissolving a biocompatible polymer in a polymer solvent to form a polymer solution, dispersing particles of biologically active, aggregation-stabilized EPO in the polymer solution, and then solidifying the polymer to form a polymeric matrix containing a dispersion of said EPO.

The advantages of this sustained release formulation for EPO include longer, more consistent in vivo blood levels of EPO, lower initial bursts of EPO, and increased therapeutic benefits by eliminating fluctuations in serum EPO levels. The advantages also include increased patient compliance and acceptance by reducing the required number of injections. The advantages further include the ability to use smaller amounts of EPO compared to bolus injection regimen because serum EPO levels are maintained closer to therapeutical thresholds.

DETAILED DESCRIPTION OF THE INVENTION

Figure 1:
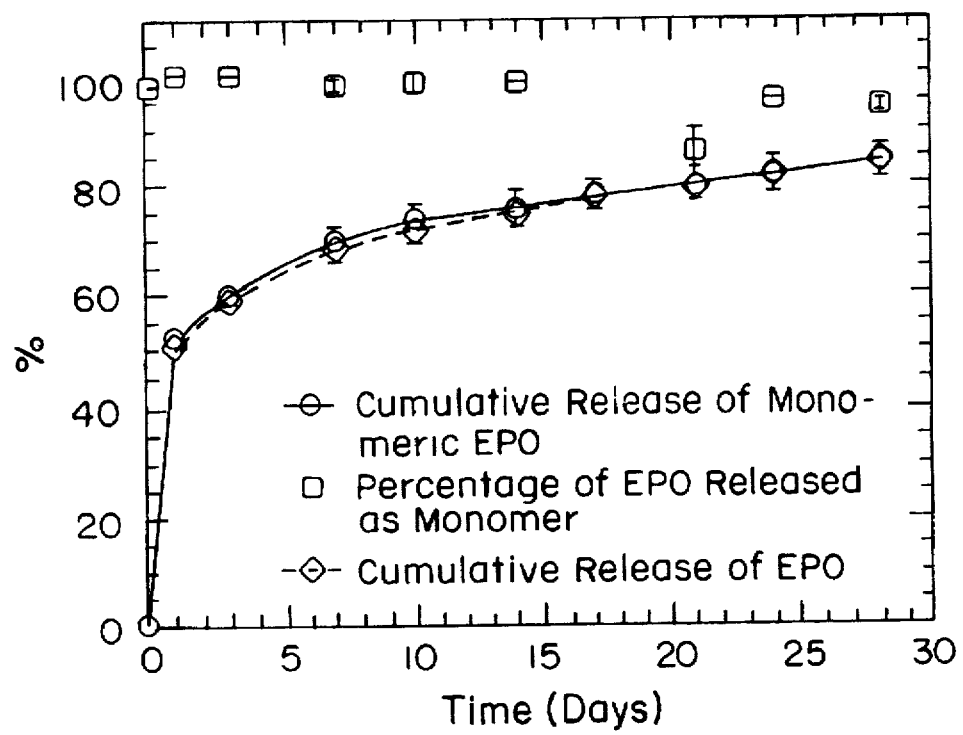
FIG. 1 is a plot of a) the cumulative release of monomeric EPO, b) the cumulative release of EPO (monomer EPO plus aggregated EPO), and c) the percentage of EPO which is released as a monomer during the interval between an indicated time point and the immediately preceding time point, in vitro in HEPES buffer, from microspheres of unblocked poly(lactide-co-glycolide) polymer (PLGA) (10,000 Dalton MW), containing 10% (w/w) $MgCO_3$ and 5% (w/w) of the Am1 formulation of Example 1, versus time over a 28 day interval.

Erythropoietin (EPO), as defined herein, includes all forms of EPO, such as EPO-α and EPO-β. EPO can be derived from animal sources or recombinantly produced as described in U.S. Pat. No. 4,703,008.

The EPO used in this invention is biologically active EPO in its molecular (monomeric or non-aggregated) form. Monomeric EPO is typically non-immunogenic.

EPO molecules which aggregate may not be biologically active in stimulating red blood cell production. Furthermore, aggregated EPO may induce an immune response resulting in antibodies formed against EPO. This may compromise the efficacy of long-term EPO therapy. Additionally, aggregated EPO may stimulate an auto-immune response to endogenous EPO.

A sustained release of biologically active, non-aggregated erythropoietin is a release which results in measurable serum levels of biologically active, monomeric EPO over a period longer than that obtained following direct administration of aqueous EPO. It is preferred that a sustained release be a release of EPO for a period of about a week or more, and more preferably for a period of about two weeks or more.

A sustained release of biologically active, non-aggregated EPO from a polymeric matrix can be continuous or non-continuous release with relatively constant or varying rates of release. The continuity of EPO released and level of EPO released can be established by using, inter alia, one or more types of polymer compositions, EPO loadings, and/or selection of excipients to produce the desired effect.

Aggregation-stabilized erythropoietin, as defined herein, comprises biologically active, monomeric EPO which is aggregation-stabilized by at least one anti-aggregation agent. In one embodiment, a class of materials, or combination of materials, suitable as anti-aggregation agents includes materials which reduce the solubility of the EPO in aqueous fluids, such as PBS, HEPES or bodily fluids (e.g., lymph), to maintain a localized concentration of EPO below the concentration at which significant aggregation of EPO molecules occurs. A localized concentration of EPO, as defined herein, is the concentration of solvated EPO within, between or immediately surrounding the sustained release microparticles, or device.

In another embodiment, suitable anti-aggregation agent include carbohydrates which prevent significant aggregation of EPO monomer for undetermined reasons.

Significant aggregation is defined as an amount of aggregation resulting in aggregation of about 10% or more of the initial amount of encapsulated EPO monomer. Preferably, aggregation is maintained below about 5% of the initial dose of EPO monomer. More preferably, aggregation is maintained below about 2% of the initial dose. Further discussion of the levels of aggregation observed for the sustained release composition of the present invention is provided in Examples 3 and 4.

In one embodiment, an anti-aggregation agent reduces EPO solubility by precipitating the EPO from the aqueous solution, thereby maintaining a suitably low localized EPO concentration. Suitable materials for precipitating a protein, without denaturing the protein, include salts which are in the Hofmeister series of precipitants of serum globulins (or "salting-out salts") as described in by Thomas E. Creighton in *Proteins: Structures and Molecular Principles*, p149–150 (published by W. H. Freeman and Company, New York). Suitable salting-out salts for use in this invention include, for example, salts containing one or more of the cations $Mg^{+2}$, $Li^+$, $Na^+$, $K^+$ and $NH_4^+$; and also contain one or more of the anions $SO_4^{-2}$, $HPO_4^{-2}$, acetate, citrate, tartrate, $Cl^-$, $NO_3^-$, $ClO_3^-$, $I^-$, $ClO_4^-$ and $SCN^-$.

In another embodiment, an anti-aggregation agent comprises at least one carbohydrate, such as mannitol.

The suitability of candidate anti-aggregation agents for stabilizing EPO against aggregation can be determined by one of ordinary skill in the art by performing a variety of stability indicating techniques such as SEC, polyacrylamide gel electrophoresis (PAGE) and potency tests on protein obtained from EPO particles containing the anti-aggregation agent and for the duration of release from the sustained release composition, as described in Example 3.

Suitable particles of biologically active, aggregation-stabilized erythropoietin are solid particles, including lyophilized particles, freeze-dried particles, pressed pellets, and particles formed by any other means known in the art for forming a solid particle from a mixture of two components (e.g., EPO and an anti-aggregation agent) wherein one component is temperature sensitive.

Wherein the biologically active, aggregation-stabilized EPO is lyophilized, it is preferred that said EPO also contain a buffer to maintain pH in a range which will prevent a significant loss of biological activity resulting from pH changes during lyophilization. Suitable pH conditions typically include pH values between about 4.0 and about 8.0. A preferred pH range is between about 5.0 and about 7.0. Suitable pH conditions are typically achieved through use of an aqueous buffer, such as sodium bicarbonate. Examples of preferred buffers include phosphate buffers, citrate buffers and combinations thereof.

The EPO particle can also contain other excipients, such as stabilizers and bulking agents. Stabilizers are added to maintain the potency of the EPO over the duration of EPO release. Suitable stabilizers include, for example, carbohydrates, amino acids, fatty acids and surfactants and are known to those skilled in the art. The amount of stabilizer used is based on ratio to the EPO on a weight basis. For amino acids, fatty acids and carbohydrates, such as sucrose, maltose, inulin, dextran and heparin, the mass ratio of carbohydrate to EPO is typically between about 1:1 and about 20:1. For surfactants, such as TWEEN™ and PLURONIC™, the mass ratio of surfactant to EPO is typically between about 0.01:1 and about 1:1.

Bulking agents typically comprise inert materials. Suitable bulking agents are known to those skilled in the art.

Polymers suitable to form a polymeric matrix of the sustained release composition of this invention are biocompatible polymers which can be either a biodegradable or non-biodegradable polymer, or blends or copolymers thereof.

Biodegradable, as defined herein, means the composition will degrade or erode in vivo to form smaller chemical species. Degradation can result, for example, by enzymatic, chemical and physical processes. Suitable biocompatible, biodegradable polymers include, for example, poly (lactides), poly(glycolides), poly(lactide-co-glycolides), poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polycyanoacrylates, poly (p-dioxanone), poly(alkylene oxalate)s, biodegradable polyurethanes, blends and copolymers thereof. Biocompatible, non-biodegradable polymers suitable for the modulated release composition of this invention include non-biodegradable polymers selected from the group consisting of polyacrylates, polymers of ethylene-vinyl acetates and other acyl substituted cellulose acetates, non-degradable polyurethanes, polystyrenes, polyvinyl chloride, polvinyl fluoride, poly(vinyl imidazole), chlorosulphonate polyolefins, polyethylene oxide, blends and copolymers thereof.

A polymer, or polymeric matrix, is biocompatible if the polymer, and any degradation products of the polymer, are non-toxic to the recipient and also present no significant deleterious or untoward effects on the recipient's body, such as an immunological reaction at the injection site.

Further, the terminal functionalities of a polymer can be modified. For example, polyesters can be blocked, unblocked or a blend of blocked and unblocked polymers. A blocked polymer is as classically defined in the art, specifically having blocked carboxyl end groups. Generally, the blocking group is derived from the initiator of the polymerization and is typically an alkyl group. An unblocked polymer is as classically defined in the art, specifically having free carboxyl end groups.

Acceptable molecular weights for polymers used in this invention can be determined by a person of ordinary skill in the art taking into consideration factors such as the desired polymer degradation rate, physical properties such as mechanical strength, and rate of dissolution of polymer in solvent. Typically, an acceptable range of molecular weights is of about 2,000 Daltons to about 2,000,000 Daltons. In a preferred embodiment, the polymer is a biodegradable polymer or copolymer. In a more preferred embodiment, the polymer is a poly(lactide-co-glycolide) (hereinafter "PLGA") with a lactide:glycolide ratio of about 1:1 and a molecular weight of about 5,000 Daltons to about 70,000 Daltons. In an even more preferred embodiment, the molecular weight of the PLGA used in the present invention has a molecular weight of about 10,000 Daltons.

The amount of EPO, which is contained in a dose of sustained release microparticles, or in an alternate sustained release device, containing biologically active, aggregation-stabilized EPO particles is a therapeutically or prophylactically effective amount, which can be determined by a person of ordinary skill in the art taking into consideration factors such as body weight, condition to be treated, type of polymer used, and release rate from the polymer.

In one embodiment an EPO sustained release composition will contain from about 0.01% (w/w) to about 50% (w/w) of biologically active, aggregation-stabilized EPO particles. The amount of such EPO particles used will vary depending upon the desired effect of the EPO, the planned release levels, the times at which EPO should be released, and the time span over which the EPO will be released. A preferred range of EPO particle loading is between about 0.1% (w/w) to about 30% (w/w) EPO particles. A more preferred range of EPO particle loading is between about 0.1% (w/w) to about 10% (w/w) EPO particles. The most preferred loading of the biologically active, aggregation-stabilized EPO particles is about 5% (w/w).

In yet another embodiment, an EPO sustained release composition also contains a biocompatible metal cation component, which is not contained in the biologically active, aggregation-stabilized EPO particles, but is dispersed within the polymer.

A metal cation component, as defined herein, is a component containing at least one kind of multivalent metal cation (having a valence of +2 or more) in a non-dissociated state, a dissociated state, or a combination of non-dissociated and dissociated states. Suitable metal cation components include, for instance, metal salts, metal hydroxides, and basic (pH of about 7 or higher) salts of weak acids wherein the salt contains a metal cation. It is preferred that the metal cation be divalent.

A metal cation component is biocompatible if it is non-toxic to the recipient, in the quantities used, and also presents no significant deleterious or untoward effects on the recipient's body, such as an immunological reaction at the injection site.

The metal cation component can optionally contain cation species and/or anion species which is contained in an anti-aggregation agent in the EPO particles. The metal cation component acts to modulate the release of the EPO from the polymeric matrix of the sustained release composition and can also enhance the stability of EPO in the composition. In a modulated EPO release, at least one EPO release characteristic, such as the EPO initial release level, the subsequent EPO release levels, duration of release and/or the amount of EPO released, is different from the release characteristics exhibited by EPO being released from a polymeric matrix, wherein the polymeric matrix does not contain a dispersed metal cation component.

A metal cation component used in modulating release typically comprises at least one type of multivalent metal cations. Examples of metal cation components suitable to modulate EPO release, include, or contain, for instance, $Mg(OH)_2$, $MgCO_3$ (such as $4MgCO_3 \cdot Mg(OH)_2 \cdot 5H_2O$), $ZnCO_3$ (such as $3Zn(OH)_2 \cdot 2ZnCO_3$), $CaCO_3$, $Zn_3(C_6H_5O_7)_2$, $Mg(OAc)_2$, $MgSO_4$, $Zn(OAc)_2$, $ZnSO_4$, $ZnCl_2$, $MgCl_2$ and $Mg_3(C_6H_5O_7)_2$. A suitable ratio of metal cation component-to-polymer is between about 1:99 to about 1:2 by weight. The optimum ratio depends upon the polymer and the metal cation component utilized. A polymeric matrix containing a dispersed metal cation component to modulate the release of a biologically active agent from the polymeric matrix is further described in co-pending U.S. patent application No. 08/237,057, filed May 3, 1994 and co-pending PCT patent application PCT/US95/05511, the teachings of which are incorporated herein by reference in their entirety.

In yet another embodiment, at least one pore forming agent, such as a water soluble salt, sugar or amino acid, is included in the microparticle to modify the microstructure of the microparticle. The proportion of pore forming agent added to the polymer solution is between about 1% (w/w) to about 30% (w/w) It is preferred that at least one pore forming agent be included in a nonbiodegradable polymeric matrix of the present invention.

An EPO sustained release composition of this invention can be formed into many shapes such as a film, a pellet, a cylinder, a disc or a microparticle. A microparticle, as defined herein, comprises a polymeric component having a diameter of less than about one millimeter and having particles of biologically active, aggregation-stabilized EPO dispersed therein. A microparticle can have a spherical, non-spherical or irregular shape. It is preferred that a microparticle be a microsphere. Typically, the microparticle will be of a size suitable for injection. A preferred size range for microparticles is from about 1 to about 180 microns in diameter, such as for injection through a 23-gauge needle.

In the method of this invention for forming a composition for the sustained release of biologically active, non-aggregated EPO, a suitable amount of biologically active, aggregation-stabilized EPO particles are dispersed within a polymer solution. The EPO particles can be dispersed by stirring, agitation, sonication or by other known mixing means. The polymer solution, having a dispersion of biologically active, aggregation-stabilized EPO is then solidified, by appropriate means, to form an EPO sustained release composition of this invention.

Alternately, biologically active, aggregation-stabilized EPO particles and a polymer can be mixed into a polymer solvent sequentially, in reverse order, intermittently, separately or through concurrent additions, to form a dispersion of the EPO particles in a polymer solution.

A suitable polymer solution contains between about 1% (w/w) and about 30% (w/w) of a suitable biocompatible polymer, wherein the biocompatible polymer is typically dissolved in a suitable polymer solvent. Preferably, a polymer solution contains about 2% (w/v) to about 20% (w/v) polymer. A polymer solution containing 5% to about 10% (w/w) polymer is most preferred.

A suitable polymer solvent, as defined herein, is solvent in which the polymer is soluble but in which the aggregation-stabilized EPO particles are substantially insoluble and non-reactive. Examples of suitable polymer solvents include polar organic liquids, such as methylene chloride, chloroform, ethyl acetate and acetone.

The preparation of EPO sustained release microparticles of the present invention is further described in Example 2.

To prepare biologically active, aggregation-stabilized EPO particles, EPO is mixed in a suitable aqueous solvent with at least one suitable anti-aggregation agent to form a stabilizing mixture, wherein each component of the stabilizing mixture can be in suspension or solution, or a combination thereof.

In forming a stabilizing mixture, the content of anti-aggregation aggregation agent is typically between about 10% (w/w) and about 80% (w/w) of the total solids in EPO particles and is preferentially more than about 40% (w/w).

It is understood that the EPO can be in a solid or a dissolved state, prior to being contacted with the anti-aggregation agent. It is also understood that the anti-aggregation agent can be in a solid or a dissolved state, prior to being contacted with the EPO. In a preferred embodiment, an aqueous solution of EPO is mixed with an aqueous solution of the anti-aggregation agent to form a stabilizing mixture.

The stabilizing mixture is then formed into particles of biologically active, aggregation-stabilized erythropoietin. Any method can be used which is known in the art for forming a solid particle from a mixture of two components wherein one component is temperature sensitive. For example, a solvated stabilizing mixture can be evaporated, lyophilized or freeze-dried. A solid stabilizing mixture can be pressed into pellets.

In a more preferred embodiment, the stabilizing mixture is a solrated mixture which is buffered with an amount of buffer which will maintain pH in a range which will prevent a significant loss of biological activity resulting from pH changes during particle formation (e.g., during lyophilization). Typically, the content of buffer to EPO in a stabilizing mixture is between about 5% (w/w) and about 20% (w/w) of the total solids. Suitable solvents are those in which the EPO and the anti-aggregation agent are each at least slightly soluble, such as in an aqueous sodium bicarbonate buffer or in an aqueous phosphate buffer. For aqueous solvents, it is preferred that water used be either deionized water or water-for-injection.

The stabilizing mixture is usually buffered to a pH between about 4.0 and about 8.0. A preferred pH range is between about 5.0 and about 7.0. Suitable pH conditions are typically achieved through use of an aqueous buffer, such as sodium bicarbonate. More preferred buffers include phosphate buffers, citrate buffers and combinations thereof.

A suitable pH range can be achieved by dialysis with a buffer, by using the buffer as a solvent for the EPO and/or anti-aggregation agent, and by making one or more bulk additions of buffer to the EPO solution before, during, and/or after addition of the anti-aggregation agent.

A solvated stabilizing mixture is then dried, such as by lyophilization, to form particles of biologically active, aggregation-stabilized EPO. The stabilizing mixture can be bulk dried or can be divided into smaller volumes which are then dried.

In a preferred embodiment, the stabilizing mixture is micronized, such as by use of an ultrasonic nozzle, frozen and then lyophilized to form biologically active, aggregation-stabilized EPO particles.

In another preferred embodiment, a stabilizing mixture is a buffered solution comprising EPO, ammonium sulfate (about 6 grams to about 8 grams of ammonium sulfate per gram of EPO) and a buffer solution (about 5 grams to about 30 grams of buffer solution per gram of EPO) with a pH between about 5 and about 7. More preferably, the buffer solution is a 5 mM citrate/5 mM phosphate buffer or 5 mM phosphate buffer (pH 7).

Preferably, particles of aggregation-stabilized EPO are between about 1 to about 6 micrometers in diameter. The EPO particles can be fragmented separately, as described in co-pending U.S. patent application No. 08/006,682, filed Jan. 21, 1993, which describes a process for producing small particles of biologically active agents, which is incorporated herein in its entirety by reference. Alternately, the EPO particles can be fragmented after being added to a polymer solution, such as by means of an ultrasonic probe or ultrasonic nozzle.

The synthesis of biologically active, aggregation-stabilized EPO particles is further described in Example 1. Additional description of microspheres containing particles of biologically active, aggregation-stabilized EPO and their release pharmacokinetics and pharmacodynamics is provided in Examples 2–5.

In yet another embodiment of the method of this invention, a metal cation component, not contained in EPO particles, is also dispersed within the polymer solution to modulate the release of EPO.

It is understood that a metal cation component and the aggregation-stabilized EPO particles can be dispersed into a polymer solution sequentially, in reverse order, intermittently, separately or through concurrent additions.

Alternately, a polymer, a metal cation component and the aggregation-stabilized EPO and can be mixed into a polymer solvent sequentially, in reverse order, intermittently, separately or through concurrent additions.

The method for forming a composition for modulating the release of a bibiologically active agent from a biodegradable polymer is further described in co-pending U.S. patent application No. 08/237,057 and co-pending PCT patent application PCT/US95/05511.

Further description of microspheres containing particles of aggregation-stabilized EPO and a metal cation component is provided in Example 2.

One suitable method for solidifying a polymer solution to form a polymeric matrix, containing particles of aggregation-stabilized EPO, is the solvent evaporation method described in U.S. Pat. No. 3,737,337, issued to Schnoring et al., U.S. Pat. No. 3,523,906, issued to Vranchen et al., U.S. Pat. No. 3,691,090, issued to Kitajima et al., or U.S. Pat. No. 4,389,330, issued to Tice et al, which are incorporated herein in their entirety by reference. Solvent evaporation can be used to form microparticles or other shaped EPO sustained release devices.

In the solvent evaporation method, a polymer solution containing an aggregation-stabilized EPO particle dispersion, is mixed in or agitated with a continuous phase, in which the polymer solvent is partially miscible, to form an emulsion. The continuous phase is usually an aqueous solvent. Emulsifiers are often included in the continuous phase to stabilize the emulsion. The polymer solvent is then evaporated over a period of several hours or more, thereby solidifying the polymer to form a polymeric matrix having a dispersion of aggregation-stabilized EPO particles contained therein. In this method, care must be taken not to heat the polymer solution to a temperature at which denaturing of the EPO in the EPO particles could occur. Further discussion of the high level of biological activity, typically >98%, maintained in the microparticles of the present invention is provided in Example 2.

Another suitable method for solidifying a polymer solution to form a polymeric matrix, containing particles of aggregation-stabilized EPO, is the phase separation method described in U.S. Pat. No. 4,675,800, which is incorporated herein in its entirety by reference. In this method, polymer within a polymer solution containing aggregation-stabilized EPO particles is precipitated around the EPO particles by the addition of a polymer non-solvent to the polymer solution to form an emulsion, wherein the polymer non-solvent is immiscible with the polymer solvent.

A preferred method for forming aggregation-stabilized EPO microparticles from a polymer solution uses rapid freezing and solvent extraction, as described in U.S. Pat. No. 5,019,400, issued to Gombotz et al. and co-pending U.S. patent application No. 08/443,726, filed May 18, 1995, the teachings of which are incorporated herein by reference in their entirety. This method of microsphere formation, as compared to other methods, such as phase separation, additionally reduces the amount of EPO required to produce a sustained release composition with a specific EPO content. Also see Example 2 for additional descriptions of microparticle formulations by this method.

In this method, the polymer solution, containing the EPO particle dispersion, is processed to create droplets, wherein at least a significant portion of the droplets contain polymer solution and biologically active, aggregation-stabilized EPO particles. These droplets are then frozen by means suitable to form microparticles. Examples of means for processing the polymer solution dispersion to form droplets include directing the dispersion through an ultrasonic nozzle, pressure nozzle, Rayleigh jet, or by other known means for creating droplets from a solution.

Means suitable for freezing droplets to form microparticles include directing the droplets into or near a liquified gas, such as liquid argon and liquid nitrogen to form frozen microdroplets which are then separated from the liquid gas. The frozen microdroplets are then exposed to a liquid non-solvent, such as ethanol, or ethanol mixed with hexane or pentane. The solvent in the frozen microdroplets is extracted as a solid and/or liquid into the non-solvent to form biologically active, aggregation-stabilized EPO containing microparticles. Mixing ethanol with other non-solvents, such as hexane or pentane, can increase the rate of solvent extraction, above that achieved by ethanol alone, from certain polymers, such as poly(lactide-co-glycolide) polymers.

A wide range of sizes of EPO sustained release microparticles can be made by varying the droplet size, for example, by changing the ultrasonic nozzle diameter. If very large microparticles are desired, the microparticles can be extruded through a syringe directly into the cold liquid. Increasing the viscosity of the polymer solution can also increase microparticle size. For example, the size of the microparticles produced by this process can range from greater than 1000 to 1 micrometers or less in diameter.

Yet another method of forming an EPO sustained release composition from a polymer solution, includes film casting, such as in a mold, to form a film or a shape. For instance, after putting the polymer solution containing a dispersion of aggregation-stabilized EPO particles into a mold, the polymer solvent is then removed by means known in the art, or the temperature of the polymer solution is reduced, until a film or shape, with a consistent dry weight, is obtained. Film casting of a polymer solution, containing a biologically active agent, is further described in co-pending U.S. patent application No. 08/237,057.

The method of this invention for forming a biologically active EPO sustained release composition can also ba used to form a sustained release composition of other biologically active agents which are soluble in aqueous solutions and at sufficiently high concentrations in solution, have a tendency to aggregate to form biologically inactive polymers.

It is believed that the release of the EPO can occur by two different mechanisms. The EPO can be released by diffusion through aqueous filled channels generated in the polymeric matrix, such as by the dissolution of the EPO or by voids created by the removal of the polymer's solvent during the synthesis of the sustained release composition. The rate of polymer hydrolysis may be increased by non-neutral pH's. Therefore, an acidic or a basic excipient can be added to the polymer solution, used to form the microparticle, to alter the polymer erosion rate.

The second mechanism is the release of EPO due to degradation of the polymer. The rate of degradation can be controlled by changing polymer properties that influence the rate of hydration of the polymer. These properties include, for instance, the ratio of different monomers, such as lactide and glycolide, comprising a polymer; the use of the L-isomer of a monomer instead of a racemic mixture; the end groups and the molecular weight of the polymer. These properties can affect hydrophilicity and crystallinity, which control the rate of hydration of the polymer. Hydrophilic excipients such as salts, carbohydrates and surfactants can also be incorporated to increase hydration and which can alter the rate of erosion of the polymer.

By altering the properties of the polymer, the contributions of diffusion and/or polymer degradation to EPO release can be controlled. For example, decreasing the molecular weight of the polymer, using an unblocked polymer instead of a blocked polymer, or increasing the glycolide content of a poly(lactide-co-glycolide) polymer can enhance the hydrolysis of the polymer and thus provide an increased EPO release from polymer erosion. The effects of different molecular weight unblocked PLGA polymers are further described in Example 5.

The sustained release composition of this invention can be administered to a human, or other animal, by injection, implantation (e.g. subcutaneously, intramuscularly, intraperitoneally, intracranially, intravaginally and intradermally), administration to mucosal membranes (e.g., intranasally or by means of a suppository), or in situ delivery (e.g. by enema or aerosol spray) to provide the desired dosage of EPO based on the known parameters for treatment with EPO of the various medical conditions.

The invention will now be further and specifically described by the following examples.

EXAMPLE 1

Preparation of Biologically Active, Aggregation-Stabilized Erythropoietin

Erythropoietin was derived as described in U.S. Pat. No. 4,703,008. The EPO was dissolved in deionized water to form an aqueous solution having a concentration of approximately 1 mg/ml. Different samples of the EPO solution were then dialyzed against three changes of the appropriate formulation buffer (i.e., 5 mM phosphate buffer (pH 7), 5 mM citrate buffer (pH 7), 5 mM citrate/5 mM phosphate buffer (pH 7) or 10 mM bicarbonate buffer (pH 7)).

Following dialysis, the concentration of EPO in the dialyzed solutions was verified to be approximately 1 mg/ml as determined by measuring absorbance at 280 nm ($\epsilon$=1.345 L $gm^{-1}$ $cm^{-1}$).

Portions of the dialyzed EPO solutions were then mixed with concentrated solutions of candidate anti-aggregation agents (i.e., ammonium sulfate, zinc acetate, mannitol/sucrose or mannitol/maltose) to form the EPO formulations provided in Table I below. The candidate anti-aggregation agent solutions also possibly contained additional excipients (i.e. inulin, glycine and TWEEN 20™ surfactant).

The anti-aggregation agent solutions were separately prepared in the same buffers used to dialyze the EPO solutions to which they were subsequently added.

Approximate volumes of each anti-aggregation agent solution and of additional buffer were added to a 50 ml polypropylene tube to achieve the desired concentrations for the formulations (described in Table I). Each dialyzed EPO solution was then added to the appropriate anti-aggregation agent solution and then the solutions were mixed by gentle inversion.

TABLE I

| Formulations (wt %) | Am1 | Am4 | Am7 | Ma1 | Ma3 | Ma4 | Zn1 | Zn6 |
|---|---|---|---|---|---|---|---|---|
| EPO | 10.0 | 10.1 | 9.9 | 10.0 | 10.0 | 10.0 | 10.0 | 10.0 |
| Ammonium Sulfate | 66.8 | 64.7 | 79.1 | 0.0 | 0.0 | 0.0 | 0.0 | 0.0 |
| Zinc Acetate | 0.0 | 0.0 | 0.0 | 0.0 | 0.0 | 0.0 | 76.9 | 76.9 |
| Mannitol | 0.0 | 0.0 | 0.0 | 62.5 | 62.5 | 72.5 | 0.0 | 0.0 |
| Sucrose | 0.0 | 0.0 | 0.0 | 10.0 | 0.0 | 10.0 | 0.0 | 0.0 |
| Maltose | 0.0 | 0.0 | 0.0 | 0.0 | 10.0 | 0.0 | 0.0 | 0.0 |
| 5 mM Citrate Buffer (pH 7) | 0.0 | 15.1 | 0.0 | 0.0 | 0.0 | 0.0 | 0.0 | 0.0 |
| 5 mM Phosphate Buffer (pH 7) | 0.0 | 0.0 | 10.0 | 7.5 | 7.5 | 7.5 | 0.0 | 0.0 |
| 5 mM Citrate/ 5 mM Phosphate Buffer (pH 7) | 22.1 | 0.0 | 0.0 | 0.0 | 0.0 | 0.0 | 0.0 | 0.0 |
| 10 mM Bicarbonate Buffer (pH 7) | 0.0 | 0.0 | 0.0 | 0.0 | 0.0 | 0.0 | 13.1 | 12.1 |
| Inulin | 1.1 | 10.1 | 1.0 | 0.0 | 0.0 | 0.0 | 0.0 | 0.0 |
| Glycine | 0.0 | 0.0 | 0.0 | 10.0 | 10.0 | 0.0 | 0.0 | 0.0 |
| TWEEN 20™ Surfactant | 0.0 | 0.0 | 0.0 | 0.0 | 0.0 | 0.0 | 0.0 | 1.0 |

Each of the formulated EPO solutions were aspirated into a 60 ml plastic syringe fitted with Teflon tubing and then atomized through an ultrasonic nozzle (Type V1A; Sonics and Materials, Inc., Danbury, Conn.) into polypropylene containers containing liquid nitrogen, making sure that the atomized material was fully submerged at all times, to form frozen particles. The container was kept at −80° C. until the liquid nitrogen was entirely evaporated. The frozen particles, which contained biologically active, aggregation-stabilized EPO, were transferred into glass beakers then lyophilized to form biologically active, aggregation-stabilized EPO particles. The EPO particles were removed from the lyophilizer under an atmosphere of dry nitrogen, handled in a low humidity environment, and stored desiccated at −80° C.

EXAMPLE 2

Preparation of PLGA Microspheres Containing Biologically Active, Aggregation-Stabilized Erythropoietin Microspheres containing the aggregation-stabilized EPO formulations of Example 1 were prepared from unblocked (50:50; MW 10,000 Daltons) PLGA, obtained from Boehringer Ingelheim Chemicals, Inc., Montvale, N.J., or blocked (50:50; MW 10,000 Daltons) PLGA obtained from Birmingham Polymers, Inc., Birmingham, Ala.

In addition, microspheres, containing the Am7 formulation of aggregation-stabilized EPO particles, were prepared from unblocked (50:50) PLGA with a molecular weight of approximately 31,000 Daltons or 45,000 Daltons, (Boehringer Ingelheim Chemicals, Inc., Montvale, N.J.).

The method described in Gombotz et al. (U.S. Pat. No. 5,019,400) was used to encapsulate the aggregation-stabilized EPO particles of Example 1 in PLGA. In each case, polymer was dissolved in 5.1 ml of methylene chloride to form a polymer solution. Magnesium carbonate, or zinc carbonate, was sieved through a 38 micrometer sieve and was then added to the polymer solution to a final concentration of 10% w/vol. The polymer/salt suspension was subsequently combined with 30 mg of aggregation-stabilized EPO particles.

The polymer solution, containing suspended salt and EPO particles, was placed in an ice-water bath and sonicated using an ultrasonic probe (Virtis Co., Gardiner, N.Y.) to reduce the protein particle size to approximately 2 to 3 micrometers in diameter and to form a dispersion of EPO particles within the polymer solution.

A frozen bed of ethanol was prepared in a polypropylene tub by surrounding the tub with liquid nitrogen, then covering the frozen ethanol with additional liquid nitrogen. The EPO/polymer suspension was then pumped at a rate of 1–2 ml/min from a syringe by a syringe pump (Orion Research Inc., Boston, Mass.) into an ultrasonic nozzle placed above the container of frozen ethanol and liquid nitrogen. The EPO/polymer suspension was atomized into droplets which froze upon contact with the liquid nitrogen and formed microspheres which sank to the surface to the frozen ethanol.

The container was placed at −80° C. to evaporate the liquid nitrogen and allow the ethanol to melt. As the ethanol thawed, the microspheres sank into the ethanol and the methylene chloride was extracted from the microspheres. After 24 hours, additional ethanol, which was prechilled to −80° C., was added to the container. Two days after the microspheres were prepared, the ethanol/microsphere slurry was filtered through a 0.65 micron Durapure® membrane (Millipore, Bedford, Mass.) using a precooled filter apparatus. The filtration was performed in a glove box that was preflushed with nitrogen gas. The filtered microspheres were then lyophilized (on a shelf that had been precooled to −40° C.) until dry.

The immunoreactivity of the EPO in these sustained release microspheres was subsequently determined by extracting protein and analyzing by radioimmunoassay (RIA) (Incstar: Stillwater, Minn.). To extract the EPO from the microspheres, approximately 10 mg of microspheres were placed in a tube with 250 μl of methylene chloride. The samples were vortexed for 10 to 20 seconds and left at room temperature for 5 minutes to dissolve the polymer. A sample of acetone (750 μl) was added, vortexed for an additional 10 seconds, and centrifuged at 14,000 rpm for 30 seconds at 4

° C. to pellet the EPO. The spernatent was removed and the methylene chloride and acetone steps were repeated twice more. Samples were dried in a lyophilizer or vacuum oven for 14-18 hours at room temperature. The EPO pellet was reconstituted in 1 ml HEPES buffer by vortexing for about 10 seconds, then standing at room temperature for about 1 hour until completely dissolved. The extracted EPO was diluted in buffer (8.1 mM $Na_2HPO_4$, 1.5 mM $KH_2PO_4$, 400 mM NaCl, pH 7.5) to a concentration of approximately 25 µg/ml for analysis.

The immunoreactivity of the EPO was found to be 121,000±5000 units per mg of EPO. This specific activity is comparable to the range obtained for bulk EPO (130,000-140,000 units per mg of EPO, thus showing an insignificant reduction of EPO activity due to the method of forming the sustained release compositions of the present invention. Monomer content was found to be greater that 98% for all microspheres.

The microspheres containing Am1 and Am7 EPO particles were also assayed for EPO dimer, by size exclusion chromatography (SEC), and for high molecular weight EPO aggregates by SDS-PAGE/Western blot analysis No EPO dimer or high molecular weight aggregates were detected.

EXAMPLE 3

In Vitro Release of EPO From Aggregation-Stabilized Particles Within PLGA Microspheres The in vitro release kinetics of EPO from aggregation-stabilized particles within PLGA microspheres were assessed in HEPES buffer (75 mM HEPES, 115 mM NaCl, 0.1% (by volume) TWEEN 20™, 0.1% (by weight) sodium azide titrated to pH 7.4 with NaOH) or in HEPES buffer containing 2% or 20% sheep serum. The serum containing buffer is 80% by volume above plus 20% by volume sheep serum. The studies were conducted by suspending 8-10 mg of microspheres in 1-5 ml of buffer at 37° C. At specified time points, the buffer was removed in full and replaced with fresh buffer.

Figure 2:
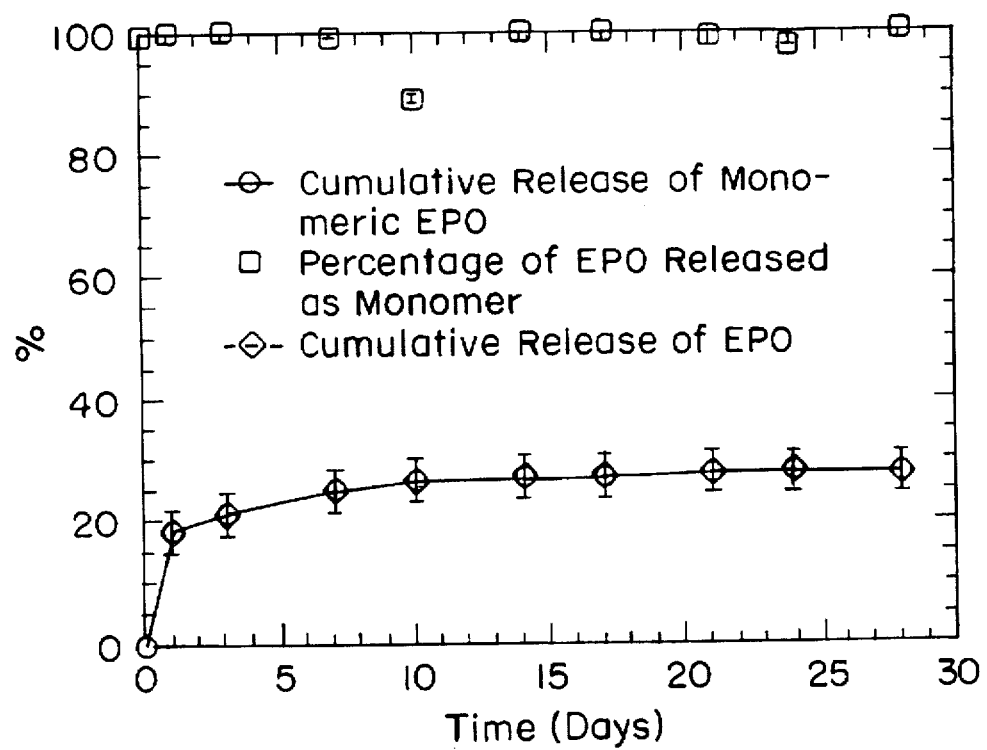
FIG. 2 is a plot of a) the cumulative release of monomeric EPO, b) the cumulative release of EPO (monomer or aggregate), and c) the percentage of EPO which is released as a monomer, in vitro in HEPES buffer, from microspheres unblocked PLGA (10,000 Dalton MW), containing 10% (w/w) MgCO3 and 5% (w/w) of the Am7 formulation of Example 1, versus time over a 28 day interval.

In samples incubated in HEPES buffer, the releases over time of EPO monomer (biologically active EPO) and of EPO aggregates (biologically inactive EPO) were determined by size exclusion chromatography (SEC). The results of the SEC analyses upon in vitro release kinetics in HEPES buffer of various microspheres, wherein the microspheres were a) unblocked PLGA (MW 10,000 Daltons) microspheres containing formulations Am1 or Am7, and b) blocked PLGA (MW 10,000 Daltons) microspheres containing Zn1, are provided in FIGS. 1, 2 and 3, respectively. FIGS. 1 and 2 show the EPO released from formulations containing ammonium sulfate as an anti-aggregation agent was almost all monomeric EPO over the length of the release period.

Figure 3:
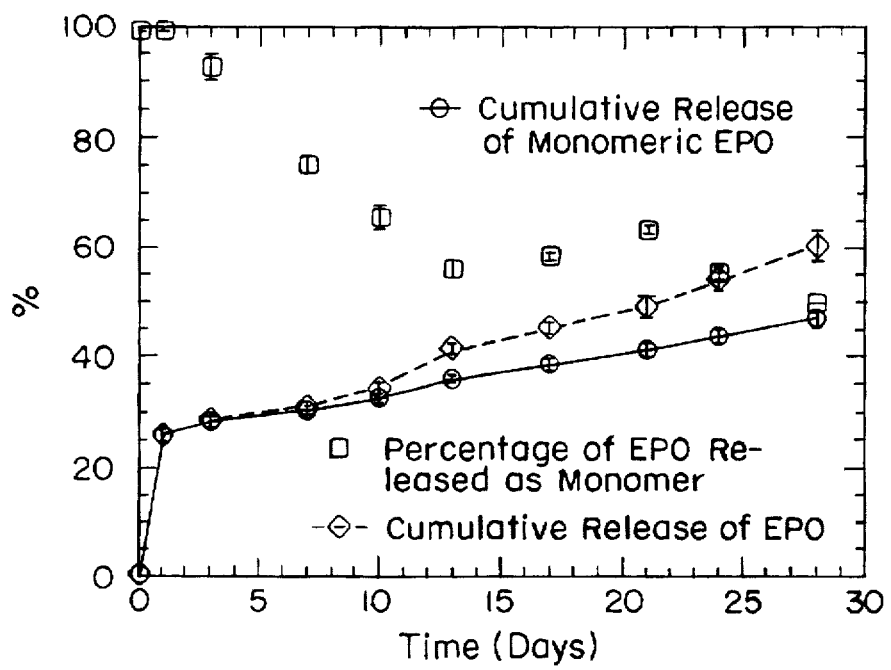
FIG. 3 is a plot of a) the cumulative release of monomeric EPO, b) the cumulative release of EPO (monomer or aggregate), and c) the percentage of EPO which is released as a monomer, in vitro in HEPES buffer, from microspheres of blocked PLGA (10,000 Dalton MW), containing 10% (w/w) ZnCO3 and 10% (w/w) of the Zn1 formulation of Example 1, versus time over a 28 day interval.

FIG. 3 shows the EPO released from a formulation containing zinc acetate, as an anti-aggregation agent, contained significant levels of aggregate which increased substantially over the length of the release period.

The results of the SEC and RIA analyses upon in vitro release kinetics in HEPES buffer, and in HEPES/serum, of various microspheres (all in 10,000 Dalton PLGA) which contained different EPO formulations of Example 1 are provided in Table II. The initial burst and release rate were determined in the HEPES/serum test by RIA. The integrity of the released EPO was assessed in HEPES buffer by SEC.

TABLE II

| Formula | EPO Load (%) | Polymer/ Salt | Aggregate Released (% init. load) | Initial Burst (%) | Average Release (%/day) | Release Duration (days) |
|---|---|---|---|---|---|---|
| Zn1 | 10 | Blocked/ 10% $MgCO_3$ | 12 | 66 | 1.2 | 14 |
| Zn1 | 10 | Blocked/ 10% $ZnCO_3$ | 22 | 46 | 1.7 | 28 |
| Zn6 | 10 | Blocked/ 10% $ZnCO_3$ | 37 | 32 | 1.6 | 28 |
| Am1 | 5 | Unblocked/ 10% $MgCO_3$ | 1 | 39 | 1.4 | 21 |
| Am1 | 10 | Blocked/ 10% $MgCO_3$ | 2 | 71 | 0.3 | 3 |
| Am4 | 5 | Unblocked/ 10% $MgCO_3$ | 1 | 29 | 1.1 | 21 |
| Am4 | 5 | Unblocked/ none | 1 | 35 | 0.9 | 28 |
| Ma1 | 5 | Unblocked/ 10% $MgCO_3$ | 1 | 44 | 1.8 | 24 |
| Ma3 | 10 | Unblocked/ 10% $MgCO_3$ | 1 | 71 | 1.3 | 21 |
| Ma4 | 10 | Blocked/ 10% $ZnCO_3$ | 1 | 77 | 0.6 | 3 |

These analyses show that the addition of suitable anti-aggregation agents significantly reduced the aggregation of EPO over the release periods. These analyses also demonstrated that the addition of a metal cation component (e.g., salt) to the polymer, as well as the selection of the type of polymer (i.e., blocked or unblocked) significantly affected the initial burst level and the duration of release.

EXAMPLE 4

Integrity of EPO Released from Ammonium Sulfate Aggqregation-Stabilized EPO Particles Within PLGA Microspheres The purpose of the experiment was to determine the integrity of EPO released from microshperes having varying concentrations of ammonium sulfate.

Aggregation-stabilized EPO formulations comparable to AM7, except having 10%, 20%, or 40% ammonium sulfate, were prepared as described in Example 1. The eliminated ammonium sulfate was replaced with sodium chloride or sucrose such that the total weight of ammonium sulfate and sodium chloride or sucrose was 79%.

The percent monomeric and aggregate EPO were determined after 35 days and 42 days release in vitro. The AM7 formulation, as well as the 40% ammonium sulfate/NaCl formulation produced 3-4% aggregates at both time points, whereas the 10% and 20% ammonium sulfate/NaCl formulations produced 5-6% aggregates. Mannitol formulations produced results similar to the 10% and 20% ammonium sulfate formulations.

In the case where ammonium sulfate was replaced with sucrose, there was not sufficient drug released from the 40% ammonium sulfate formulation to quantitate. The 10% and 20% ammonium sulfate formulations with sucrose, like their sodium chloride counterparts, showed more aggregates (6-9%) than were observed with the AM7 formulation.

EXAMPLE 5

Effect of Co-Administered Cyclosporin and Hydrocortisone on In Vivo Pharmacokinetics of Erythropoietin Male Sprague-Dawley rats, weighing 400±50 g (S.D.), were used as the animal model. The rats were not fasted before the experiments and subsequently were fed with a standard diet, an iron supplement, and allowed free access to water. Iron dextran (Sigma Co., St. Louis, Mo.) 5 mg/kg was injected intraperitoneally twice a week.

These experiments utilized the method described in co-pending U.S. patent application No. 08/480,813 abandoned, filed Jun. 7, 1995, Attorney Docket No. ACT95-03, of suppressing antibody production in the test animals in response to the EPO released (or injected) to obtain accurate profiles of serum EPO levels. Therein, antibody production is suppressed by administration of cyclosporin A and hydrocortisone to the test animal.

A purpose of the first experiment was to compare the in vivo pharmacodynamic effects of EPO released from sustained release microspheres to EPO injected subcutaneously as a bolus, specifically upon serum reticulocyte profiles. Two groups of, three rats were injected subcutaneously in the interscapular region on day 0 with 10,000 units of RMAm7 EPO microspheres (unblocked 10K PLGA containing 10% $MgCO_3$ and 5% Am7) and subsequently on day 28 with a 2,000 unit bolus of aqueous EPO. The control group did not receive the cyclosporin A/hydrocortisone therapy, which the test group did receive.

Blood samples were taken from the tail vein of each rat at 1, 3, 4, 8, 10, 14, 16, 20, 24, 28, 30 or 31, 32 and 36 hours after injection. Additional blood samples were then taken approximately once a day for the following 4–5 days.

Figure 4:
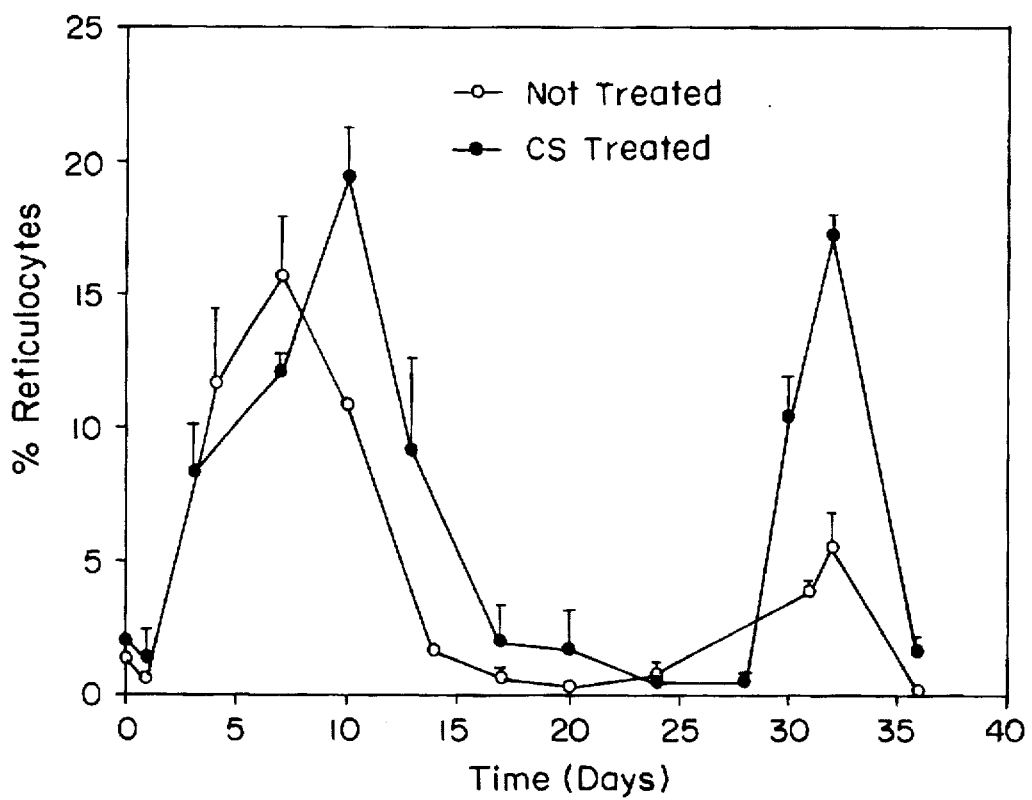
FIG. 4 is a plot of the percent reticulocytes in blood of CS/HC treated and untreated rats, which were subcutaneously injected with 10,000 units of the EPO sustained release microspheres RMAm7, described in Example 5 on day 0 a bolus of 2,000 units of aqueous EPO, administered on day 28, versus time over a 36 day interval.

Blood reticulocyte levels were counted for each blood sample. The results are provided in FIG. 4. FIG. 4 shows higher reticulocyte counts in immunosuppressed rats in response to both the EPO microspheres and the EPO bolus. The non-immunosuppressed rats (control group) showed lower reticulocyte levels due to antibody formation resulting from the immune systems' responses to EPO. This is particularly shown by the lack of a significant increase in reticulocyte levels in the control group after receiving the EPO bolus on day 28.

FIG. 4 also shows that injection with sustained release microspheres resulted in a longer period of elevated serum reticulocyte levels than did a bolus of EPO.

A purpose of the second experiment was to compare the in vivo pharmacokinetic and pharmacodynamic effects of EPO released from various sustained release microspheres.

The rats in each of four groups rats (N=3) were injected subcutaneously in the interscapular region with one of four of the following formulations of microspheres:

| | |
|---|---|
| RMAm1 | Unblocked 10 K PLGA/10% $MgCO_3$/5% Am1 |
| RMMa1 | Unblocked 10 K PLGA 10% $MgCO_3$/5% Ma1 |
| PZZn1 | Blocked 10 K PLGA/10% $ZnCO_3$/5% Zn1 |
| RMAm7 | Unblocked 10 K PLGA/10% $MgCO_3$/5% Am7 |

Each rat received between 10,000 to 12,000 units per animal. Each rats was also given daily an intraperitoneal injection of 10 mg cyclosporin A (Sandimmune® Injection, Sandoz, East Hanover, N.J.) and 5 mg hydrocortisone (Spectrum Co., Gardena, Calif.) in 0.5 ml sterilized saline for injection (USP) for days 0 to 14 and then injections twice a week for days 15 to 28. These injections were to suppress the response of the rats' immune systems to EPO.

Blood samples were taken from the tail vein of each rat at 1, 2, 4, 8, 10 (optionally), 24, 36 and 48 hours after injection. Additional blood samples were then taken approximately once a day for the following 4–5 days. The EPO concentration in the rat serum samples was determined using by ELISA. In addition, blood reticulocyte levels were counted.

Figure 5:
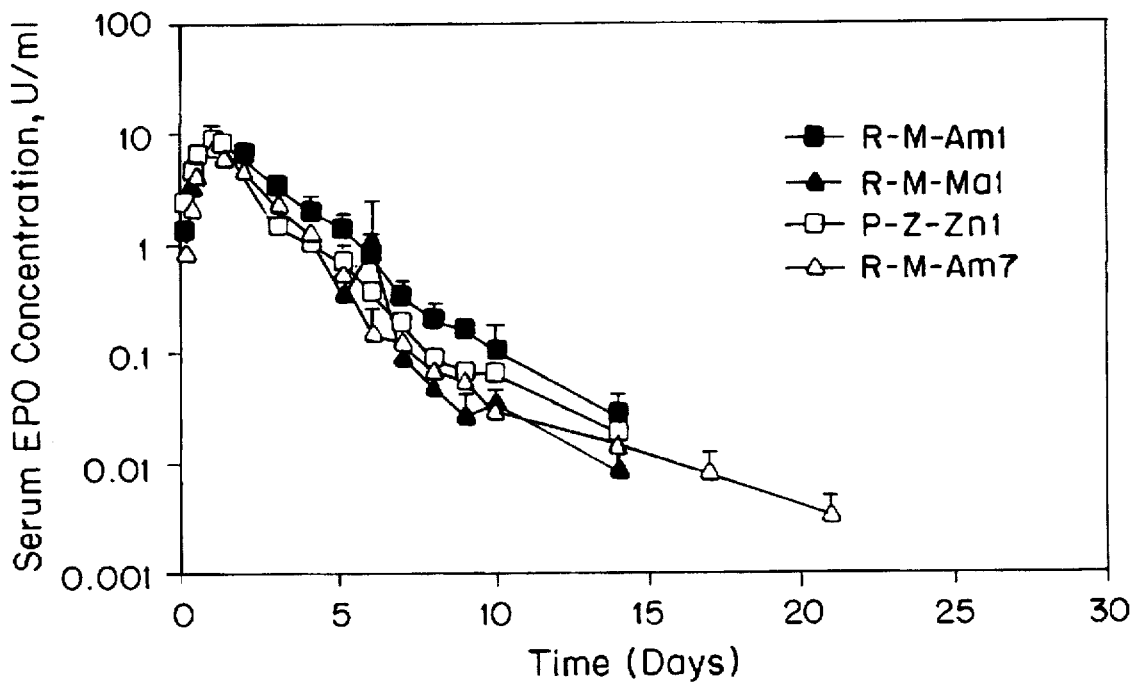
FIG. 5 is a plot of the serum concentration (IU/ml) of EPO in rats, which were subcutaneously administered various EPO sustained release microspheres, described in Example 3, versus time over a 22 day interval.
Figure 6:
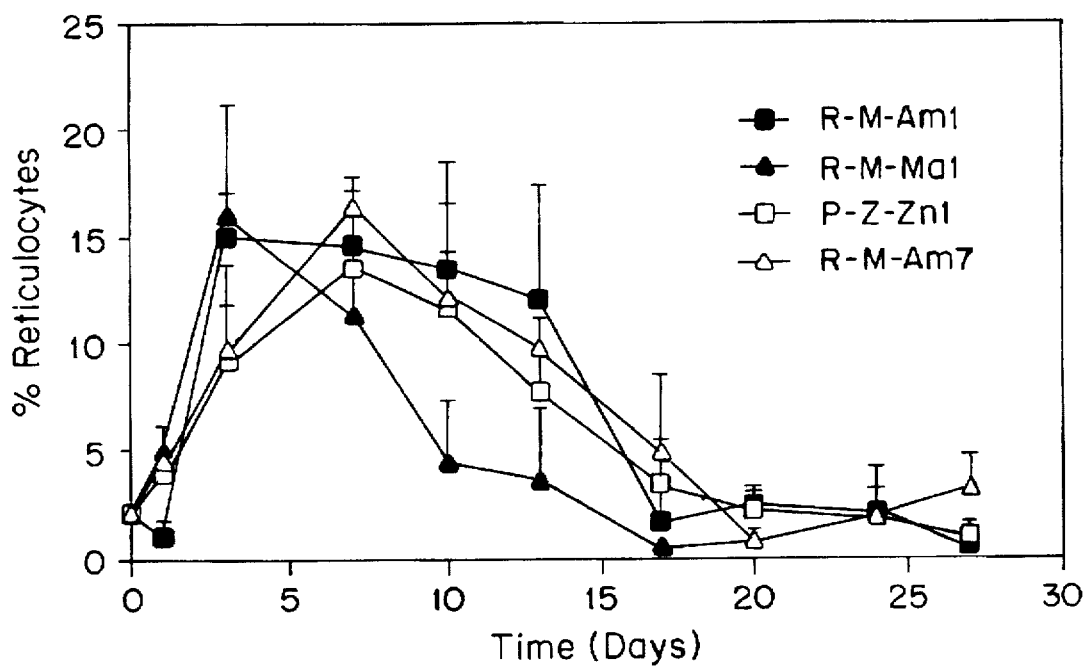
FIG. 6 is a plot of the percent reticulocytes in blood of rats, which were subcutaneously injected with 10,000 units of various EPO sustained release microspheres, described in Example 3, versus time over a 28 day interval.

Serum EPO and blood reticulocyte profiles for these formulations are provided in FIGS. 5 and 6. EPO levels remained above baseline in these animals for approximately 14 days, showing a sustained release of biologically active EPO. Elevated reticulocyte levels were observed for about 17 days. Further, the response of immature and total reticulocyte levels were proportional and not significantly different from each other following EPO treatment.

EXAMPLE 6

Effect of Polymer Molecular Weight on EPO Release in Rats

Rats (N=3) in three test groups were injected, as described in Example 4, with the microspheres of Example 2, having the Am7 EPO particle formulation, in different molecular weight PLGA polymers (10,000 Daltons, 31,000 Daltons or 45,000 Daltons). The dose for each rat was about 10,000 units.

The purpose of the test was to determine the effects of polymer molecular weight upon sustained EPO release levels and release period.

Figure 7:
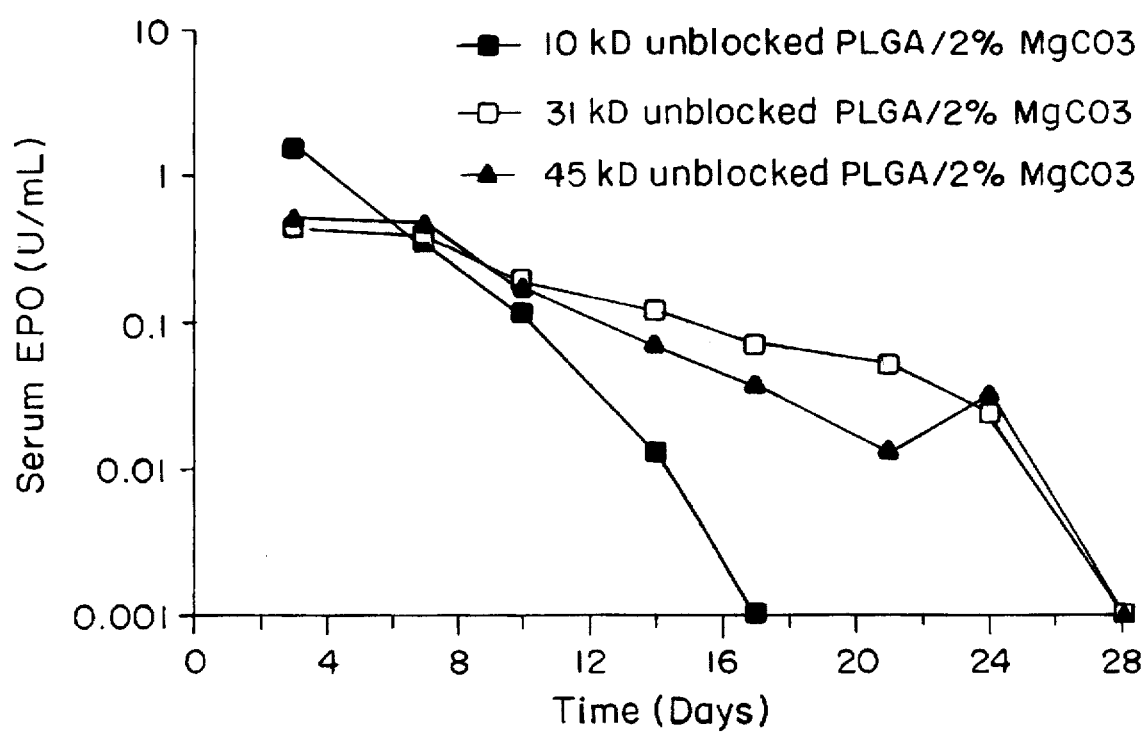
FIG. 7 is a plot of the serum concentration (IU/ml) of EPO in rats which were subcutaneously injected with 10,000 units of microspheres of Example 2, containing the AM7 formulation of Example 1 in unblocked PLGA polymers having molecular weights of a) 10,000 Daltons, b) 31,000 Daltons or c) 48,000 Daltons, versus time over a 28 day interval.

Blood samples were taken from the tail vein of each rat on days 3, 7, 10, 14, 17, 21, 24 and 28 after injection. The EPO concentration in the rat serum samples was determined using by ELISA. The results are provided in FIG. 7. FIG. 7 shows that substantially decreasing polymer molecular weight increases the rate of EPO release and shortens the release period in unblocked PLGA containing 2% $MgCO_3$.

EQUIVALENTS

Those skilled in the art will recognize, or be able to ascertain, using no more than routine experimentation, many equivalents to specific embodiments of the invention described specifically herein. Such equivalents are intended to be encompassed in the scope of the following claims.

The invention claimed is:

1. A composition for the sustained release of biologically active, non-aggregated erythropoietin from a polymeric matrix, comprising:

a) a biodegradable polymer; and b) particles of biologically active, aggregation-stabilized erythropoietin, wherein said particles include erythropoietin in contact with a salting-out salt, and wherein said erythropoietin particles are dispersed within the polymeric matrix.

2. A sustained release composition of claim 1 wherein the salting-out salt comprises a salt containing a cation selected from the group consisting of $Mg^{+2}$, $Li^+$, $Na^+$, $K^+$, $NH_4^+$ and combinations thereof.

3. A sustained release composition of claim 1 wherein the salting-out salt comprises a salt containing an anion selected from the group consisting of $SO_4^{-2}$, $HPO_4^{-2}$, acetate, titrate, tartrate, $Cl^-$, $NO_3^-$, $ClO_3^-$, $I^-$, $ClO_4^-$, $SCN^-$ and combinations thereof.

4. A sustained release composition of claim 1 wherein the salting-out salt is ammonium sulfate.

5. A sustained release composition of claim 1 wherein the biodegradable polymer is selected from the group consisting of poly(lactides), poly(glycolides), poly(lactide-co-glycolides), poly(lactic acid)s, poly(glycolic acid)s; poly(lactic acid-co-glycolic acid)s, polycaprolactone, polycarbonates, polyesteramides, polyanhydrides, poly(amino acids), polyorthoesters, polycyanoacrylates, poly(p-dioxanone), poly(alkylene oxalate)s, biodegradable polyurethanes, blends and copolymers thereof.

6. A sustained release composition of claim 5 wherein said polymer comprises poly(lactide-co-glycolide).

7. A sustained releage composition of claim 1 further comprising a metal cation component, wherein the metal cation component is not contained in said erythropoietin particles, and wherein the metal cation component is dispersed within the biodegradable polymer to modulate the release of erythropoietin from the polymeric matrix.

8. A sustained release composition of claim 7 wherein the metal cation component is selected from the group consisting of magnesium hydroxide, magnesium carbonate, calcium carbonate, zinc carbonate, magnesium acetate, zinc acetate, magnesium sulfate, zinc sulfate, magnesium chloride, zinc chloride, zinc citrate, magnesium citrate and combinations thereof.

9. A composition for the sustained release of biologically active, non-aggregated erythropoietin from a polymeric matrix, comprising:
   a) unblocked poly(lactide-co-glycolide) with a molecular weight of at least about 10,000 Daltons;
   b) particles of biologically active, aggregation-stabilized erythropoietin, wherein said particles include erythropoietin in contact with a salting-out salt, wherein the percentage of weight of the composition attributable to said erythropoietin particles is about 5%, and wherein said erythropoietin particles are dispersed within the polymeric matrix; and
   c) magnesium carbonate particles dispersed in the polymeric matrix, in an effective amount.

10. A composition of claim 9 wherein the salting-out salt is present at a concentration of at least about 10% of the total solids in the erythropoietin particles.

11. A method for forming a composition for the sustained release of biologically active erythropoietin from a polymeric matrix, comprising the steps of:
   a) dissolving a biodegradable polymer in a polymer solvent to form a polymer solution;
   b) dispersing particles of biologically active, aggregation-stabilized erythropoietin in the polymer solution, wherein said particles include erythropoietin in contact with a salting-out salt; and
   c) solidifying the polymer to form a polymeric matrix containing a dispersion of said erythropoietin particles.

12. A method of claim 11 wherein the salting-out salt comprises a salt containing an anion selected from the group consisting of $SO_4^{-2}$, $HPO_4^{-2}$, acetate, citrate, tartrate, $Cl^-$, $NO_3^-$, $ClO_3^-$, $I^-$, $ClO_4^-$, $SCN^-$ and combinations thereof.

13. A method of claim 11 wherein the salting-out salt comprises a salt containing a cation selected from the group consisting $Mg^{+2}$, $Li^+$, $Na^+$, $K^+$, $NH_4^+$ and combinations thereof.

14. A method of claim 11 wherein the salting-out salt is ammonium sulfate.

15. The method of claim 11 further comprising the step of dispersing a metal cation component within the polymer solution, wherein the metal cation component is not contained in the erythropoietin particles.

16. A method of claim 15 wherein the metal cation component is multivalent.

17. A method of claim 16 wherein the metal cation component is selected from the group consisting of magnesium hydroxide, magnesium carbonate, calcium carbonate, zinc carbonate, magnesium acetate, zinc acetate, magnesium sulfate, zinc sulfate, magnesium chloride, zinc chloride, zinc citrate, magnesium citrate and combinations thereof.

18. A method for forming microparticles for the sustained release of biologically active, non-aggregated erythropoietin, comprising the steps of:
   a) mixing biologically active erythropoietin with a salting-out salt and with a buffer, wherein said buffer has a pH between about 4 and about 8, to form an aggregation-stabilizing mixture; and
   b) lyophilizing said mixture to form biologically active, aggregation-stabilized erythropoietin;
   c) dispersing particles of biologically active, aggregation-stabilized erythropoietin in a polymer solution to form a dispersion;
   d) freezing droplets of the dispersion to form microparticles; and
   e) contacting the microparticles with a liquid non-solvent, which is miscible with the polymer solvent, whereby the polymer solvent is extracted from the microparticles, thereby forming microparticles for the sustained release of biologically active, non-aggregated erythropoietin.

19. The method of claim 18 wherein the salting-out salt is ammonium sulfate.

20. Biologically active, aggregation-stabilized erythropoietin, comprising a lyophilizate of a solution containing:
   a) biologically active erythropoietin;
   b) a salting-out salt; and
   c) a buffer with a pH between about 4 and about 8.

21. A biologically active, aggregation-stabilized erythropoietin of claim 20 wherein the salting-out salt comprises a salt containing an anion selected from the group consisting of: $SO_4^{-2}$, $HPO_4^{-2}$, acetate, citrate, tartrate, $Cl^-$, $NO_3^-$, $ClO_3$, $I^-$, $ClO_4^-$, $SCN^-$ and combination thereof.

22. A biologically active, aggregation-stabilized erythropoietin of claim 20 wherein the salting-out salt comprises a salt containing a cation selected from the group consisting of $Mg^{+2}$, $Li^+$, $Na^+$, $K^+$, $NH_4^+$ and combinations thereof.

23. A biologically active, aggregation-stabilized erythropoietin of claim 20 wherein the salting-out salt is ammonium sulfate.

24. A method for providing a therapeutically effective blood level of biologically active, non-aggregated erythropoietin in a subject for a sustained period, comprising administering to the subject a dose of the sustained release composition of claim 1.

25. A method of claim 24 wherein the salting-out salt comprises a salt containing a cation selected from the group consisting of $Mg^{+2}$, $Li^+$, $Na^+$, $K^+$, $NH_4^+$ and combinations thereof.

26. A method of claim 24 wherein the salting-out salt comprises a salt containing an anion selected from the group consisting of $SO_4^{-2}$, $HPO_4^{-2}$, acetate, citrate, tartrate, $Cl^-$, $NO_3^-$, $ClO_1^-$, $I^-$, $ClO_4^-$, $SCN^-$ and combinations thereof.

27. A method of claim 24 wherein the salting-out salt is ammonium sulfate.

28. A method of claim 24 wherein the biologically active, aggregation-stabilized erythropoietin particles are formed by lyophilizing a solution containing:
   a) biologically active erythropoietin;
   b) a salting-out salt; and
   c) a buffer with a pH between about 4 and about 8.

29. A method of claim 28 wherein the salting-out salt is ammonium sulfate.

* * * * *

UNITED STATES PATENT AND TRADEMARK OFFICE
CERTIFICATE OF CORRECTION

| | | |
|---|---|---|
| PATENT NO. | : | 5,674,534 |
| DATED | : | October 7, 1997 |
| INVENTOR(S) | : | Stephen E. Zale, Paul A. Burke, Howard Bernstein and Avram Brickner |

It is certified that error appears in the above-identified patent and that said Letters Patent is hereby corrected as shown below:

In Column 16, line 54:   After the word "acetate", delete "titrate" and insert therefor --citrate--;

In Column 17, line 3:   After the word "sustained", delete "releage" and insert therefor --release--;

In Column 17, line 47:   After "$HPO_4^{-2}$," delete "acetate citrate" and insert therefor --acetate, citrate--.

Signed and Sealed this

Sixteenth Day of December, 1997

Attest:

BRUCE LEHMAN

Attesting Officer            Commissioner of Patents and Trademarks